United States Patent [19]

Miura et al.

[11] Patent Number: 5,025,012
[45] Date of Patent: Jun. 18, 1991

[54] NICOTINIC ACID DERIVATIVES AND PHARMACEUTICAL COMPOSITIONS COMPRISING SAME

[75] Inventors: Katsutoshi Miura; Hiroyasu Koyama; Toshiji Sugai; Hiroaki Yamada; Einosuke Sakurai, all of Saitama, Japan

[73] Assignee: Nisshin Flour Milling Co., Ltd., Tokyo, Japan

[21] Appl. No.: 484,130

[22] Filed: Feb. 22, 1990

[30] Foreign Application Priority Data

Mar. 1, 1989 [JP] Japan .................................. 1-46647

[51] Int. Cl.$^5$ ................... A61K 31/495; A61K 31/44; A61K 31/445; C07D 410/04
[52] U.S. Cl. .................................. 514/252; 514/211; 514/212; 514/218; 514/235.5; 514/316; 540/544; 540/575; 540/597; 544/124; 544/131; 544/360; 544/364; 546/187; 546/193; 546/194
[58] Field of Search ............... 544/124, 360, 364, 131; 540/575, 544, 597; 546/193, 194, 187; 514/252, 218, 316, 318, 235.5, 211, 212,

[56] References Cited

FOREIGN PATENT DOCUMENTS 230402 11/1989 European Pat. Off. .
8807528 10/1988 Int'l Pat. Institute .
125083 11/1976 Japan .
286968 12/1987 Japan .

OTHER PUBLICATIONS

Delarge et al., Chem. Abst. 77-88325h (1972).
Nagano et al., Chem. Abst. 108-150164u (1988).
Organic Synthesis, vol. 3, 723-725.

Primary Examiner—Cecilia Shen
Attorney, Agent, or Firm—Abelman Frayne Rezac & Schwab

[57] ABSTRACT

Compounds are disclosed of the formula

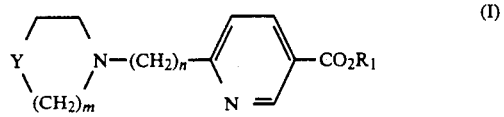

(I)

wherein
$R_1$ is hydrogen or $C_1$–$C_6$ alkyl;
Y is —$CH_2$—, —O—,

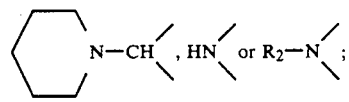

$R_2$ is $C_1$–$C_6$ alkyl; $C_2$–$C_6$ alkenyl; $C_3$–$C_6$ cycloalkyl; phenyl which may be mono- or di-substituted on the phenyl ring with $C_1$–$C_6$ alkoxy; aralkyl which may be mono- or di-substituted on the aromatic ring with $C_1$–$C_6$ alkoxy; diphenylmethyl; carboalkoxy; or an O- or N-heterocyclic radical which is linked to the nitrogen atom via carbonyl or carbonylmethylene;
m is 2 or 3;
and n is 0 or 1, and physiologically acceptable acid addition salts thereof. The compounds of formula (I) are of a blood flow-increasing action and can be used for the therapy or prevention of diseases in the cardiovascular system.

12 Claims, No Drawings

NICOTINIC ACID DERIVATIVES AND PHARMACEUTICAL COMPOSITIONS COMPRISING SAME

FIELD OF THE INVENTION

The present invention relates to new derivatives of nicotinic acid or an ester thereof, a process for preparing the same and pharmaceutical compositions comprising said derivatives as an active ingredient.

The nicotinic acid derivatives and their physiologically acceptable salts of the invention are effective in the therapy and prevention of disturbances of cerebral or peripheral circulation and ischemic heart diseases to be treated by increasing blood flow.

BACKGROUND OF THE INVENTION

Japanese Patent Kokai No. 51-125083 discloses nicotinic acid derivatives of a structure in which a piperazine ring is attached to the pyridine ring as a compound having an antiinflammatory activity. However, other pharmacological activities of those derivatives are not known. Japanese Patent Kokai No. 62-286968 also discloses certain nicotinamide derivatives as a therapeutic agent for cardiovascular diseases. However, those nicotinamide derivatives are not considered to exhibit satisfactory drug action for said therapeutic agent.

Thus there is a continuing need for new compounds with more improved pharmacological activities than known nicotinic acid or amide derivatives.

The present invention results from efforts to develop new compounds having a high pharmacological activity and being commercially satisfactory.

DISCLOSURE OF THE INVENTION

According to the present invention, there are provided compounds of formula (I)

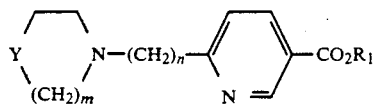

wherein
$R_1$ is hydrogen or $C_1$–$C_6$ alkyl;
Y is —$CH_2$—, —O—,

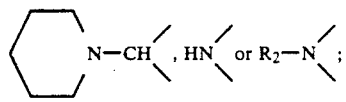

$R_2$ is $C_1$–$C_6$ alkyl, $C_2$–$C_6$ alkenyl, $C_3$–$C_6$ cycloalkyl, phenyl which may be mono- or di-substituted on the phenyl ring with $C_1$–$C_6$ alkoxy, aralkyl which may be mono- or di-substituted on the aromatic ring with $C_1$–$C_6$ alkoxy. diphenylmethyl, carboalkoxy and an O— or N-heterocyclic radical which is linked to the nitrogen atom via carbonyl or carbonylmethylene;
m is 2 or 3;
and n is 0 or 1
and physiologically acceptable acid addition salts thereof.

Examples of $R_1$ in formula (I) include hydrogen and $C_1$–$C_6$ alkyl such as methyl, ethyl, n-propyl, i-propyl, n-butyl, i-butyl, tert-butyl, hexyl.

Examples of $R_2$ in formula (I) include $C_1$–$C_6$ alkyl or $C_1$–$C_6$ alkenyl such as methyl, ethyl, n-propyl, i-propyl or propenyl; $C_3$–$C_6$ cycloalkyl such as cyclopentyl, cyclohexyl; phenyl which may be mono- or di-substituted on the phenyl ring with $C_1$–$C_6$ alkoxy such as methoxy or ethoxy; aralkyl such as benzyl or phenylethyl which may be mono- or di-substituted on the phenyl ring with $C_1$–$C_6$ alkoxy such as methoxy or ethoxy; diphenylmethyl; carboalkoxy such as methoxycarbonyl or ethoxycarbonyl; and an 0- or N-heterocyclic radical which is linked to the nitrogen atom via carbonyl or carbonylmethylene such as 2-furancarbonyl or 1-pyrrolidinylcarbonylmethyl.

Representative examples of the compounds according to the invention are as follows:
1) 6-(4-Ethoxycarbonyl-1-piperazinyl)nicotinic acid,
2) 6-(4-Methyl-1-piperazinyl)nicotinic acid,
3) 6-(4-Diphenylmethyl-1-piperazinyl)nicotinic acid,
4) 6-(1-Piperazinyl)nicotinic acid,
5) Methyl 6-(4-methyl-1-piperazinyl)nicotinate,
6) Methyl 6-(1-piperazinyl)nicotinate,
7) Methyl 6-(4-ethyl-1-piperazinyl)nicotinate,
8) Methyl 6-(4-phenyl-1-piperazinyl)nicotinate,
9) Methyl 6-(4-benzyl-1-piperazinyl)nicotinate,
10) Methyl 6-(4-o-methoxyphenyl-1-piperazinyl)nicotinate,
11) Methyl 6-[4-(3,4-dimethoxybenzyl)-1-piperazinyl]nicotinate,
12) Methyl 6-[4-(1-pyrrolidinylcarbonylmethyl)-1-piperazinyl]nicotinate,
13) Methyl 6-homopiperazinylnicotinate,
14) Ethyl 6-(1-piperazinyl)nicotinate,
15) Ethyl 6-(4-methyl-1-piperazinyl)nicotinate,
16) Isopropyl 6-(4-methyl-1-piperazinyl)nicotinate,
17) Methyl 6-(4-methyl-1-piperazinylmethyl)nicotinate,
18) Methyl 6-(4-diphenylmethyl-1-piperazinylmethyl)nicotinate,
19) Methyl 6-piperizinonicotinate,
20) Methyl 6-morpholinonicotinate,
21) Methyl 6-(4-piperizinopiperizino)nicotinate,
22) Methyl 6-(4-cyclopentyl-1-piperazinyl)nicotinate,
23) Methyl 6-(4-isobutyl-1-piperazinyl)nicotinate,
24) Methyl 6-(4-cyclohexyl-1-piperazinyl)nicotinate,
25) Methyl 6-(4-propenyl-1-piperazinyl)nicotinate,
26) Methyl 6-(4-diphenylmethyl-1-piperazinyl)nicotinate,
27) Methyl 6-[4-(2-furancarbonyl)-1-piperazinyl]nicotinate,
28) Ethyl 6-(4-diphenylmethyl-1-piperazinyl)nicotinate,
29) Ethyl 6-[4-(2-furancarbonyl)-1-piperazinyl]nicotinate, and
30) Methyl 6-(4-methyl-1-homopiperazinyl)nicotinate.

The compounds of the invention can be prepared by reacting a compound of formula (II)

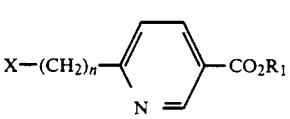

wherein $R_1$ and n are as defined above, and X is halogen with a compound of formula (III)

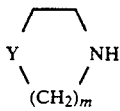

(III)

wherein Y and m are as defined above in the presence of an acid-binding agent to give a compound of formula (I)

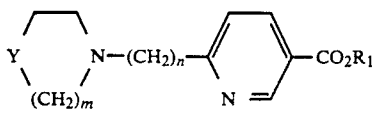

(I)

wherein $R_1$, Y, m and n are as defined above; or in the case a compound of formula (III) wherein Y is

reacting a compound of formula (I) obtained as above with a compound of formula (IV)

$$R_2X \quad (IV)$$

wherein $R_2$ and X are as defined above in the presence of an acid-binding agent; or with a mixture of formaldehyde and formic acid to give a compound of formula (I) wherein Y is

and if necessary, converting the compounds thus obtained to physiologically acceptable acid addition salts thereof.

The condensation reaction between a compound of formula (II) and a compound of formula (III) for the synthesis of the compounds of the invention and the condensation reaction between a compound of formula (I) thus obtained wherein Y is

and a compound of formula (IV) can be accomplished by a reaction in an organic solvent in the presence of an acid-binding agent at a temperature between room temperature and a reflux temperature of the solvent for a period from several minutes to tens hours.

The acid-binding agents which can be employed include inorganic basic materials such as sodium hydroxide, potassium hydroxide, ammonia, sodium carbonate and potassium carbonate and organic basic materials such as secondary amines, e.g., diisopropylamine and tertiary amines, e.g., triethylamine, methylmorpholine and pyridine, and an excess amount of the compounds of formula (III).

The reaction solvents which may be used include an alcohol such as methanol, ethanol; an aliphatic hydrocarbon such as n-hexane, petroleum ether; an aromatic hydrocarbon such as benzene, toluene, xylene; an alicyclic compound such as cyclohexane; a halogenated hydrocarbon such as carbon tetrachloride, chloroform, dichloroethane, trichloroethane; a cyclic ether such as tetrahydrofuran, dioxane; an aliphatic ester such as ethyl acetate, butyl acetate; an aliphatic ketone such as acetone or methyl ethyl ketone, N,N-dimethylformamide, dimethylsulfoxide.

Isolation of the desired compounds thus produced can be carried out by a conventional method. Thus, the desired condensation products are purified by distilling off the solvent after completion of the reaction, pouring the residue onto water, extracting the resulting mass with an organic solvent such as diethyl ether, ethyl acetate, dichloromethane, distilling off the extraction solvent from the extract and subjecting the residue to recrystallization or chromatography.

In the case where the compound of formula (I) is a carboxylic acid ($R_1=H$), crystals precipitated after cooling are filtered and dissolved in an excess of an aqueous sodium hydroxide solution, and the solution is washed with an organic solvent such as toluene and then neutralized with an acid such as concentrated hydrochloric acid. Washing with water and drying of the precipitated crystals afford the desired condensation product.

Alternatively, the compound of formula (I) wherein $R_1$ is H can also be produced by first preparing a compound of formula (I) wherein $R_1$ is $C_1$-$C_6$ alkyl and then hydrolyzing the ester group.

Furthermore, the reaction between a compound of formula (I) wherein Y is

and a mixture of formaldehyde and formic acid can proceed under reaction conditions known for the Eschweiler-Clarke reaction, for example, as described in Organic Syntheses Vol. 3, pages 723-725.

The compounds of formula (I) thus produced can be converted into acid addition salts thereof by a conventional method. The acid addition salts include acid addition salts of the compounds with an inorganic acid such as hydrochloric, sulfuric, phosphoric, hydrobromic, nitric acids, and acid addition salts of the compounds with an organic acid such as acetic, propionic, succinic, butyric, malic, citric, fumaric, tartaric acids.

The compounds of formula (I) according to the present invention have a marked blood flow-increasing action in warm-blooded animals and can be used for the therapy or prevention of diseases in the cardiovascular system. Diseases in the cardiovascular system include disturbances of cerebral or peripheral circulation and ischemic heart diseases.

Thus, the invention further relates to pharmaceutical compositions for use in the therapy or prevention of the above-mentioned diseases, which comprise as an active ingredient a compound of formula (I) or a physiologically acceptable acid addition salt thereof.

The pharmaceutical compositions of the invention can orally or parenterally be administered in the suitable dosage forms. They can be administered alone, but are generally administered with a pharmaceutical carrier selected on the basis of the chosen route of administration and standard pharmaceutical practice. The dosage forms include tablets, capsules, suppositories, troches, syrups, creams, ointments, pasters, cataplasms, granules, powders, injections, suspensions and the like. Bi- or multi-layered tablets can also be prepared in combination with other drugs. Furthermore, tablets with conventional coating applied, for example, sugar-coated tablets, tablets with enteric coating or film-coated tablets can also be prepared.

In forming solid dosage forms there can be used additives such as lactose, white sugar, crystalline cellulose, corn starch, calcium phosphate, sorbitol, glycine, carboxymethyl cellulose, gum arabic, polyvinylpyrrolidone, hydroxypropyl cellulose, glycerin, polyethylene glycol, stearic acid, magnesium stearate and talc.

In forming semi-solid dosage forms, vegetable or synthetic waxes or fats and the like are used.

In forming liquid dosage forms, there can be employed additives such as an aqueous sodium chloride solution, sorbitol, glycerin, olive oil, almond oil, propylene glycol and ethyl alcohol.

The content of the active ingredient in the above dosage forms is in the range between 0.1 and 100% by weight, suitably between 1 and 50% by weight for oral administration and between 0.1 and 10% by weight for injection.

The dosage administered will, of course, vary depending upon the mode and route of administration, age, sex and weight of the patient, nature and extent of symptoms and the like. Usually a daily dosage of active ingredient can be about 1 to 1000 mg per kg of body weight.

The invention is further illustrated by the following non-limitative examples.

EXAMPLES 1-3

Preparation of 6-(4-ethoxycarbonyl-1-piperazinyl)nicotinic acid (compound 1)

A mixture of 10.1 g of ethyl 1-piperazine carboxylate, 5.0 g of 6-chloronicotinic acid and 15 ml of xylene was stirred at 140°-150° C. for 3 hours. After cooled crystals were filtered, to the crystals was added a solution of 2.6 g of sodium hydroxide in 30 ml of water followed by extraction with toluene. Concentrated hydrochloric acid was added to the aqueous layer, and crystals precipitated were filtered, washed with water and dried to afford 7.1 g of 6-(4-ethoxycarbonyl-1-piperazinyl)nicotinic acid (yield 80%).

6-(4-Methyl-1-piperazinyl)nicotinic acid (compound 2) and 6-(4-diphenylmethyl-1-piperazinyl)nicotinic acid (compound 3) were prepared in the same way as above using 1-methylpiperazine and 1-diphenylmethylpiperazine, respectively, in place of ethyl-1-piperazine carboxylate.

EXAMPLE 4

Preparation of 6-(1-piperazinyl)nicotinic acid (compound 4)

2.8 g of 6-(4-ethoxycarbonyl-1-piperazinyl)nicotinic acid obtained in Example 1 and 2 g of potassium hydroxide were dissolved in 20 ml of water. The solution was heated under reflux for 2 hours. After cooled, the reaction mixture was neutralized with concentrated hydrochloric acid and crystals precipitated were filtered, washed with water and dried to give 1.7 g of 6-(1-piperazinyl)nicotinic acid (yield 82%).

EXAMPLES 5-21

Preparation of methyl 6-(4-methyl-1-piperazinyl)nicotinate (compound 5)

To a solution of 5.15 g of methyl 6-chloronicotinate, 3.15 g of 1-methylpiperazine and 3.18 g of diisopropylamine in 50 ml of DMF was added a catalytic amount of NaI. The mixture was heated to 120°-130° C. and stirred for 4 hours. The resulting mixture was poured into 250 ml of water followed by extraction with ethyl acetate. The extract was washed twice with water, and once with a saturated aqueous sodium chloride solution, then dried over anhydrous magnesium sulfate and concentrated. Purification of the concentrate by column chromatography (silica gel; chloroform:methanol=3:1) afforded 5.39 g of methyl 6-(4-methyl-1-piperazinyl)nicotinate (yield 77%).

The same procedure as mentioned above was repeated but replacing 1-methylpiperazine by piperazine, 1-ethylpiperazine, 1-phenylpiperazine, 1-benzylpiperazine, 1-(o-methoxyphenyl)piperazine, 1-(3,4-dimethoxybenzyl)piperazine, 1-(1-pyrrolidinylcarbonylmethyl)-piperazine and homopiperazine, respectively, to give methyl 6-(1-piperazinyl)nicotinate (compound 6), methyl 6-(4-ethyl-1-piperazinyl)nicotinate (compound 7), methyl 6-(4-phenyl-1-piperazinyl)nicotinate (compound 8), methyl 6-(4-benzyl-1-piperazinyl)nicotinate (compound 9), methyl 6-(4-(2-methoxyphenyl)-1-piperazinyl)nicotinate (compound 10), methyl 6-[4-(3,4-dimethoxybenzyl)-1-piperazinyl]nicotinate (compound 11), methyl 6-(4-(1-pyrrolidinylcarbonylmethyl)-1-piperazinyl]nicotinate (compound 12) and methyl 6-(1-homopiperazinyl)nicotinate (compound 13), respectively. Ethyl 6-(1-piperazinyl)nicotinate (compound 14), ethyl 6-(4-methyl-1-piperazinyl)nicotinate (compound 15) and isopropyl 6-(4-methyl-1-piperazinyl)nicotinate (compound 16) were also prepared in the same way as above by using a corresponding ethyl or isopropyl ester in place of methyl 6-chloronicotinate. Furthermore, methyl 6-(4-methyl-1-piperazinylmethyl)nicotinate (compound 17) and methyl 6-(4-diphenylmethyl-1-piperazinylmethyl)nicotinate (compound 18) were prepared in the same way as above by replacing methyl 6-chloronicotinate by methyl 6-chloromethylnicotinate. In addition, reaction of methyl 6-chloronicotinate with piperidine, morpholine or 4-piperidinopiperidine in the same way as above gave methyl 6-piperidinonicotinate (compound 19), methyl 6-morpholinonicotinate (compound 20) and methyl 6-(4-piperidinopiperidino)nicotinate (compound 21), respectively.

In preparing the above-mentioned compounds 6-21, reaction conditions summarized in Table 1 below were employed.

TABLE 1

| Compound | Acid binding agent | Reaction solvent | NaI catalyst | Reaction temp. | Reaction time (hr) |
| --- | --- | --- | --- | --- | --- |
| Compound 6 | * | Toluene | Presence | Reflux temp. | 8 |
| Compound 7 | Diisopropylamine | Toluene | Presence | Reflux temp. | 7 |

TABLE 1-continued

| Compound | Acid binding agent | Reaction solvent | NaI catalyst | Reaction temp. | Reaction time (hr) |
|---|---|---|---|---|---|
| Compound 8 | Diisopropylamine | Ethanol | Absence | Reflux temp. | 8.5 |
| Compound 9 | Diisopropylamine | Ethanol | Absence | Reflux temp. | 8.5 |
| Compound 10 | Diisopropylamine | Ethanol | Absence | Reflux temp. | 11 |
| Compound 11 | Diisopropylamine | DMF | Presence | 110–120° C. | 7 |
| Compound 12 | Diisopropylamine | DMF | Absence | 110–120° C. | 8 |
| Compound 13 | * | Toluene | Presence | 120–130° C. | 4 |
| Compound 14 | * | Toluene | Absence | Reflux temp. | 8 |
| Compound 15 | * | DMF | Absence | 120–130° C. | 5 |
| Compound 16 | * | DMF | Presence | 120–130° C. | 4 |
| Compound 17 | $Na_2CO_3$ | Ethanol:Chloroform = 5:2 | Absence | 50–60° C. | 3.5 |
| Compound 18 | $Na_2CO_3$ | Ethanol:Chloroform = 5:8 | Absence | 50–60° C. | 4 |
| Compound 19 | * | DMF | Presence | 110–120° C. | 7.5 |
| Compound 20 | * | DMF | Presence | 120–130° C. | 4.5 |
| Compound 21 | Diisopropylamine | Toluene | Presence | Reflux temp. | 7 |

*1-Substituted piperazines or homopiperazine was used in excess.

EXAMPLES 22–29

Preparation of methyl 6-(4-cyclopentyl-1-piperazinyl)nicotinate (compound 22)

To a solution of 2.21 g of methyl 6-piperazinylnicotinate (compound 6), 3.18 g of sodium carbonate and 1.64 g of cyclopentyl bromide in 50 ml of DMF was added a catalytic amount of NaI. The mixture was heated to 120°–130° C. and stirred for 4 hours. The resulting mixture was poured into 150 ml of water and extracted with ethyl acetate. The extract was washed twice with water, and once with a saturated aqueous sodium chloride solution, then dried over anhydrous magnesium sulfate and concentrated. Purification of the concentrate by column chromatography (silica gel; ethyl acetate) afforded 1.73 g of methyl 6-(4-cyclopentyl-1-piperazinyl)-nicotinate (yield 60%).

The same procedure as mentioned above was repeated but replacing cyclopentyl bromide by isobutyl bromide, cyclohexyl bromide, 2-propenyl bromide, diphenylmethyl bromide and 2-furoyl chloride, respectively, to give methyl 6-(4-isobutyl-1-piperazinyl)nicotinate (compound 23), methyl 6-(4-cyclohexyl-1-piperazinyl)nicotinate (compound 24), methyl 6-(4-propenyl-1-piperazinyl)nicotinate (compound 25), methyl 6-(4-diphenylmethyl-1-piperazinyl)nicotinate (compound 26) and methyl 6-[4-(2-furancarbonyl)-1-piperazinyl]nicotinate (compound 27), respectively.

Ethyl 6-(4-diphenylmethyl-1-piperazinyl) nicotinate (compound 28) and ethyl 6-[4-(2-furancarbonyl)-1-piperazinyl]nicotinate (compound 29), respectively, were also prepared in the same way as above by replacing methyl 6-piperazinylnicotinate (compound 6) by ethyl 6-piperazinylnicotinate (compound 14) and replacing cyclopentyl bromide by diphenylmethyl bromide and 2-furoyl chloride, respectively.

In preparing the above-mentioned compounds 23–29 reaction conditions summarized in Table 2 below were employed.

TABLE 2

| Compound | Acid binding agent | Reaction solvent | NaI catalyst | Reaction temp. | Reaction time (hr) |
|---|---|---|---|---|---|
| Compound 23 | $Na_2CO_3$ | DMF | Presence | 90–100° C. | 6.5 |
| Compound 24 | $Na_2CO_3$ | DMF | Presence | 120–130° C. | 18 |
| Compound 25 | $Na_2CO_3$ | DMF | Absence | 5° C–Room temp. | 2.5 |
| Compound 26 | $Na_2CO_3$ | DMF | Absence | Room temp. | 5 |
| Compound 27 | $Na_2CO_3$ | DMF | Absence | Room temp. | 4 |
| Compound 28 | $Na_2CO_3$ | DMF | Absence | Room temp. | 5 |
| Compound 29 | $Na_2CO_3$ | DMF | Absence | Room temp. | 4 |

EXAMPLE 30

Preparation of methyl 6-(4-methyl-1-homopiperazinyl)nicotinate (compound 30)

A mixture of 1.50 g of methyl 6-homopiperazinylnicotinate (compound 13), 0.68 g of 35% formaldehyde and 1.2 g of formic acid was stirred at 70°–80° C. for 2 hours. The resulting mixture was poured into 120 ml of water and extracted with ethyl acetate. The extract was washed twice with water and once with a saturated aqueous sodium chloride solution, then dried over anhydrous magnesium sulfate and concentrated. Purification of the concentrate by column chromatography (silica gel; ethyl acetate : methanol = 1:2) gave 1.35 g of methyl 6-(4-methyl-1-homopiperazinyl)nicotinate (yield 85%).

Table 3 shows the compounds 1–30 for chemical structure, yield and physical properties. In the table the NMR refers to values as measured using TMS as standard. The NMR was measured for compound 4 after converted to the Na salt.

TABLE 3

| Compound No. | Structure | Yield | m.p. (°C.) (Solvent for recrystallization) | IR $\nu_{max}$ (cm$^{-1}$) | $^1$H-NMR |
|---|---|---|---|---|---|
| 1 | pyridine-CO$_2$H with piperazine N-CO$_2$Et | 80% | 217–220 | (nujol)1718, 1698, 1675, 1606, 1430 | (CDCl$_3$) δ8.87(1H, d, J=2.2Hz), 8.09(1H, dd, J=9.0, 2.2Hz), 6.62(1H, d, J=9.0Hz), 4.19(1H, q, J=7.1Hz), 3.80–3.53(8H, m), 1.30(3H, t, J=7.1Hz) |
| 2 | pyridine-CO$_2$H with piperazine N-Me | 62% | 224–226 (Dec.) | (KBr)3425, 2928, 2694, 1709, 1612 | (DMSO-d$_6$) δ8.66(1H, s), 7.99(1H, d, J=9.3Hz), 6.97(1H, d, J=9.3Hz), 4.01–3.78(4H, m), 3.14–2.96(4H, m), 2.65(3H, s) |
| 3 | pyridine-CO$_2$H with piperazine N-CHPh$_2$ | 47% | 216–218 (Dec.) | (nujol)1668, 1595, 1504, 1452 | (CDCl$_3$) δ8.84(1H, d, J=2.0Hz), 8.02(1H, dd, J=8.9, 2.4Hz), 7.52–7.10(10H, m), 6.54(1H, t, J=8.9Hz), 4.26(1H, s), 3.75–3.60(4H, m), 2.56–2.42(4H, m) |
| 4 | pyridine-CO$_2$H with piperazine NH | 82% | 287–290 (Dec.) | (KBr)2860, 2760, 1640, 1600, 1375 | *(D$_2$O DSS) δ8.54(1H, s), 7.99(1H, d, J=8.6Hz), 6.78(1H, d, J=8.6Hz), 3.56–3.64(4H, m), 2.99–2.86(4H, m) |
| 5 | pyridine-CO$_2$Me with piperazine N-Me | 77% | 78–80 (Isopropyl ether) | (KBr)2930, 2810, 1728, 1620, 1510, 1440 | (CDCl$_3$) δ8.80(1H, d, J=2.4Hz), 8.04(1H, dd, J=9.0, 2.4Hz), 7.27(1H, d, J=9.0Hz), 3.87(3H, s), 3.81(4H, t, J=4.5Hz), 2.71–2.59(4H, m), 2.45(3H, s) |
| 6 | pyridine-CO$_2$Me with piperazine NH | 64% | 95–98 (Isopropyl ether) | (KBr)3204, 2942, 2846, 1718, 1604, 1499 | (CDCl$_3$) δ8.80(1H, d, J=2.4Hz), 8.04(1H, dd, J=9.2, 2.4Hz), 6.94(1H, d, J=9.2Hz), 3.87(3H, s), 3.67(4H, t, J=4.9Hz), 2.98(3H, t, J=4.9Hz) |
| 7 | pyridine-CO$_2$Me with piperazine N-Et | 79% | 102–104 (Isopropyl ether) | (KBr)2960, 2808, 1703, 1606, 1504 | (CDCl$_3$) δ8.79(1H, d, J=2.2Hz), 8.01(1H, dd, J=8.8, 2.2Hz), 6.59(1H, d, J=8.8Hz), 3.87(3H, s), 3.74(4H, t, J=5.3Hz), 2.57(4H, t, J=5.3Hz), 2.53(2H, q, J=7.2Hz), 1.15(3H, t, J=7.2Hz) |
| 8 | pyridine-CO$_2$Me with piperazine N-Ph | 67% | 132–134 (Hexane-ethyl acetate) | (KBr)2836, 1726, 1604, 1502, 1235 | (CDCl$_3$) δ8.82(1H, d, J=2.4Hz), 8.06(1H, dd, J=9.3, 2.4Hz), 7.36–7.23(2H, m), 7.02–6.84(3H, m), 6.64(1H, d, J=9.3Hz), 3.88(3H, s), 3.86(4H, t, J=5.1Hz), 3.30(4H, t, J=5.1Hz) |

TABLE 3-continued

| Compound No. | Structure | Yield | m.p. (°C.) (Solvent for recrystallization) | IR $\nu_{max}$ (cm$^{-1}$) | $^1$H-NMR |
|---|---|---|---|---|---|
| 9 | Phenyl-CH$_2$-N(piperazine)-pyridine-CO$_2$Me | 71% | 100-102 (Hexane-ethyl acetate) | (KBr)2946, 2814, 1716, 1611, 1512, 1254, 1120 | (CDCl$_3$) δ 8.78(1H, d, J=2.4Hz), 8.00(1H, dd, J=9.0, 2.4 Hz), 7.41–7.23(5H, m), 3.86(3H, s), 3.69(4H, t, J=5.1Hz), 3.56(2H, s), 2.54(4H, t, J=5.1Hz) |
| 10 | 2-OMe-phenyl-N(piperazine)-pyridine-CO$_2$Me | 75% | 123-125 (Hexane-ethyl acetate) | (KBr)2952, 2830, 1702, 1608, 1503, 1435, 1240 | (CDCl$_3$) δ 8.82(1H, d, J=2.4Hz), 8.04(1H, dd, J=9.0, 2.4 Hz), 7.13–6.86(4H, m), 6.64(1H, d, J=9.0Hz), 3.97–3.80(10H, m), 3.16(4H, t, J=5.1Hz) |
| 11 | 3,4-diMeO-phenyl-CH$_2$-N(piperazine)-pyridine-CO$_2$Me | 49% | 121-123 (Isopropyl ether-ethyl acetate) | (KBr)2936, 2832, 1711, 1608 | (CDCl$_3$) δ 8.78(1H, d, J=1.5Hz), 8.01(1H, dd, J=9.0, 1.5 Hz), 6.98–6.78(3H, m), 6.57(1H, d, J=9.0Hz), 3.90(3H, s), 3.88(3H, s), 3.86(3H, s), 3.69(4H, t, J=4.9Hz), 3.50(2H, s), 2.53(4H, t, J=4.9Hz) |
| 12 | cyclopentyl-C(=O)-N-CH$_2$-N(piperazine)-pyridine-CO$_2$Me | 61% | 145-147 (Ethyl acetate) | (KBr)2948, 2870, 2812, 1703, 1646, 1602, 1508, 1255 | (CDCl$_3$) δ 8.79(1H, d, J=2.4Hz), 8.01(1H, dd, J=9.3, 2.4 Hz), 6.59(1H, d, J=9.3Hz), 3.87(3H, s), 3.76(4H, t, J=5.1Hz), 3.57–3.43(4H, m), 3.21(2H, s), 2.72(4H, t, J=5.1Hz), 2.06–1.77(4H, m) |
| 13 | HN-piperidine-pyridine-CO$_2$Me | 51% | 61-63 (Hexane) | (KBr)3352, 2928, 2828, 1690, 1606, 1520 | (CDCl$_3$) δ 8.78(1H, d, J=2.4Hz), 7.99(1H, dd, J=9.0, 2.4 Hz), 6.47(1H, d, J=9.3Hz), 3.86(3H, s), 3.86–3.72(4H, m), 3.04(2H, t, J=5.4Hz), 2.85(2H, t, J=5.4Hz), 1.97–1.82(2H, m) |
| 14 | HN-piperazine-pyridine-CO$_2$Et | 88% | 42-43 (Hexane) | (KBr)2980, 2930, 2850, 1715, 1605, 1500 | (CDCl$_3$) δ 8.80(1H, d, J=2.4Hz), 8.02(1H, dd, J=9.0, 2.4 Hz), 6.57(1H, d, J=9.0Hz), 4.33(2H, q, J=7.1Hz), 3.66(4H, t, J=5.1Hz), 2.97(4H, t, J=5.1Hz), 1.37(3H, t, J=7.1Hz) |
| 15 | MeN-piperazine-pyridine-CO$_2$Et | 51% | 74-76 (Hexane) | (KBr)2936, 2800, 1711, 1605, 1254 | (CDCl$_3$) δ 8.81(1H, d, J=2.4Hz), 8.06(1H, dd, J=9.0, 2.4 Hz), 6.62(1H, d, J=9.0Hz), 4.34(2H, q, J=7.1Hz), 3.96–3.77 (4H, m), 2.84–2.64(4H, m), 2.52(3H, s), 1.37(3H, t, J=7.1Hz) |

TABLE 3-continued

| Compound No. | Structure | Yield | m.p. (°C.) (Solvent for recrystallization) | IR ν$_{max}$ (cm$^{-1}$) | $^1$H-NMR |
|---|---|---|---|---|---|
| 16 | MeN-[piperidine]-[pyridine]-CO$_2$iPr | 69% | 63-65 (Hexane) | (KBr)2976, 2942, 2808, 1704, 1604, 1379, 1248 | (CDCl$_3$) δ8.79(1H, d, J=2.4Hz), 8.02(1H, dd, J=9.3, 2.4 Hz), 6.59(1H, d, J=9.3Hz), 5.31-5.10(1H, m), 3.75(4H, t, J=5.0Hz), 2.58(4H, t, J=5.0Hz), 2.40(3H, s), 1.34(6H, d, J=6.1Hz) |
| 17 | MeN-[piperidine]-N-CH$_2$-[pyridine]-CO$_2$Me | 79% | 75-78 | (KBr)3070, 2945, 2925, 2780, 1720, 1595, 1450, 1430 | (CDCl$_3$) δ9.15(1H, s), 8.25(1H, d, J=8.3Hz), 7.52(1H, d, J=8.3Hz), 3.94(3H, s), 3.73(2H, s), 2.79-2.39(8H, m), 2.33(3H, s) |
| 18 | Ph$_2$CH-N-[piperidine]-N-CH$_2$-[pyridine]-CO$_2$Me | 85% | 148-149 | (KBr)3024, 2948, 2802, 2758, 1729, 1600, 1452, 1280 | (CDCl$_3$) δ9.13(1H, d, J=2.2Hz), 8.23(1H, dd, J=8.1, 2.2 Hz), 7.56-7.09(9H, m), 4.24(1H, s), 3.93(3H, s), 3.74(2H, s), 2.68-2.36(8H, m) |
| 19 | [piperidine]-[pyridine]-CO$_2$Me | 79% | 69-71 (Hexane) | (KBr)2940, 2852, 1702, 1606, 1508, 1248 | (CDCl$_3$) δ8.78(1H, d, J=4.2Hz), 7.98(1H, dd, J=9.0, 2.4 Hz), 6.58(1H, d, J=9.0Hz), 3.86(3H, s), 3.74-3.62(4H, m), 1.77-1.55(6H, m) |
| 20 | [morpholine]-[pyridine]-CO$_2$Me | 70% | 113-114 (Hexane-isopropyl ether) | (KBr)2958, 2866, 1727, 1614, 1504, 1117 | (CDCl$_3$) δ8.86(1H, d, J=2.4Hz), 8.05(1H, dd, J=9.0, 2.4 Hz), 6.58(1H, d, J=9.0Hz), 3.88(3H, s), 3.88-3.76(4H, m), 3.71-3.59(4H, m) |
| 21 | [cyclohexyl-piperidine]-[pyridine]-CO$_2$Me | 69% | 137-139 (Ethyl acetate-ethyl alcohol) | (KBr)2928, 2848, 1711, 1607, 1506, 1230 | (CDCl$_3$) δ8.78(1H, d, J=2.4Hz), 7.99(1H, dd, J=8.8, 2.4 Hz), 6.60(1H, d, J=8.8Hz), 4.59-4.44(2H, m), 3.86(3H, s), 3.00-2.82(4H, m), 2.69-2.46(5H, m), 2.04-1.88(2H, m), 1.74-1.48(8H, m) |
| 22 | [cyclopentyl-piperidine]-[pyridine]-CO$_2$Me | 46% | 151-153 (Isopropyl ether-ethyl acetate) | (KBr)2960, 2864, 1717, 1610, 1505, 1417, 1249, 1122 | (CDCl$_3$) δ8.79(1H, d, J=2.2Hz), 8.02(1H, dd, J=9.3, 2.2 Hz), 6.59(1H, d, J=9.3Hz), 3.87(3H, s), 3.84-3.68(4H, m), 2.78-2.53(5H, m), 2.03-1.43(8H, m) |
| 23 | i-Bu-N-[piperidine]-[pyridine]-CO$_2$Me | 70% | 99-101 (Hexane) | (KBr)2952, 2844, 1717, 1609, 1503, 1384, 1168 | (CDCl$_3$) δ8.79(1H, d, J=2.2Hz), 8.01(1H, dd, J=9.3, 2.2 Hz), 6.58(1H, d, J=9.3Hz), 3.86(3H, s), 3.69(4H, t, J=5.1Hz), 2.49(4H, t, J=5.1Hz), 2.14(2H, d, J=7.3Hz), 1.94-1.70(1H, m), 0.93(6H, d, J=6.6Hz) |

TABLE 3-continued

| Compound No. | Structure | Yield | m.p. (°C.) (Solvent for recrystallization) | IR $\nu_{max}$ (cm$^{-1}$) | $^1$H-NMR |
|---|---|---|---|---|---|
| 24 | (cyclohexyl-piperidinyl-pyridine-CO$_2$Me) | 13% | 154–156 (Isopropyl ether-ethyl acetate) | (KBr)2930, 2854, 1712, 1606, 1420, 1250 | (CDCl$_3$) δ8.78(1H, d, J=2.2Hz), 8.02(1H, dd, J=9.3, 2.2 Hz), 6.59(1H, d, J=9.3Hz), 3.87(3H, s), 3.84–3.68(4H, m), 2.80–2.64(4H, m), 2.50–2.28(1H, m), 2.02–1.12(10H, m) |
| 25 | (allyl-piperidinyl-pyridine-CO$_2$Me) | 72% | 95–97 (Hexane) | (KBr)3078, 1860, 1706, 1643, 1605, 1505 | (CDCl$_3$) δ8.79(1H, d, J=2.4Hz), 8.01(1H, dd, J=9.2, 2.4 Hz), 6.59(1H, d, J=9.2Hz), 6.01–5.78(1H, m), 5.31–5.15(2H, m), 3.87(3H, s), 3.71(4H, t, J=5.1Hz), 3.06(2H, d, J=6.6Hz), 2.55(4H, t, J=5.1Hz) |
| 26 | (Ph$_2$CH-piperidinyl-pyridine-CO$_2$Me) | 88% | 158–160 (Hexane) | (KBr)3024, 2948, 2894, 1718, 1602, 1495, 1435 | (CDCl$_3$) δ8.77(1H, d, J=2.5Hz), 7.99(1H, dd, J=8.8, 2.5Hz), 7.55–7.14(10H, m), 6.53(1H, d, J=8.8Hz), 4.26 (1H, s), 3.86(3H, s), 3.67(4H, t, J=5.1Hz), 2.49(4H, t, J=5.1Hz) |
| 27 | (furan-CO-piperidinyl-pyridine-CO$_2$Me) | 73% | 115–117 (Hexane-ethyl acetate) | (KBr)3110, 2985, 2905, 2860, 1705, 1630, 1610 | (CDCl$_3$) δ8.82(1H, d, J=2.2Hz), 8.07(1H, dd, J=9.0, 2.2 Hz), 7.52(1H, dd, J=1.8, 0.7Hz), 7.08(1H, dd, J=3.5, 0.7Hz), 6.61(1H, d, J=9.0Hz), 6.52(1H, dd, J=3.5, 1.8Hz), 4.34(2H, q, J=7.1Hz), 4.06–3.68(8H, m), 1.38(3H, t, J=7.1Hz) |
| 28 | (Ph$_2$CH-piperidinyl-pyridine-CO$_2$Et) | 88% | Oily product | ( )2980, 2820, 1715, 1608, 1505 | (CDCl$_3$) δ8.78(1H, d, J=2.5Hz), 7.99(1H, dd=8.8, 2.5Hz), 7.50–7.14(10H, m), 6.53(1H, d, J=8.8Hz), 4.28(2H, q, J=7.1 Hz), 4.26(1H, s), 3.67(4H, t, J=4.9Hz), 2.49(4H, t, J=4.9Hz), 1.35(3H, t, J=7.1Hz) |
| 29 | (furan-CO-piperidinyl-pyridine-CO$_2$Et) | 73% | 115–116 (Hexane-ethyl acetate) | (KBr)3110, 2985, 2905, 2860, 1705, 1630, 1610 | (CDCl$_3$) δ8.82(1H, d, J=2.2Hz), 8.07(1H, dd, J=9.0, 2.2 Hz), 7.52(1H, dd, J=1.8, 0.7Hz), 7.08(1H, dd, J=3.5, 0.7Hz), 6.61(1H, d, J=9.0Hz), 6.52(1H, dd, J=3.5, 1.8Hz), 4.34(2H, q, J=7.1Hz), 4.06–3.68(8H, m), 1.38(3H, t, J=7.1Hz) |
| 30 | (MeN-piperidinyl-pyridine-CO$_2$Me) | 85% | Oily product | ( )2944, 2846, 2796, 1713, 1605, 1511 | (CDCl$_3$) δ8.78(1H, d, J=2.4Hz), 7.99(1H, dd, J=9.0, 2.4 Hz), 6.45(1H, d, J=9.0Hz), 3.97–3.83(2H, m), 3.86(3H, s), 3.70(2H, t, J=6.3Hz), 2.75–2.66(2H, m), 2.62–2.52(2H, m), 2.38(3H, s), 2.10–1.96(2H, m) |

*Measured in the form of the sodium salt of compound 4.

EXAMPLE 31

Blood flow-increasing action was evaluated for the representative compounds of the invention by the method as described below.

(Experimental method)

Blood flow was measured unbloodily using an electromagnetic blood flow meter for right vertebral artery, right common carotid artery, left femoral artery and the left circumflex of coronary artery of the pentobarbital-anesthesized dog. The test compound was solved in saline and was intravenously administered at a dose of 1 mg/kg. Results of the test were expressed in terms of the percentage of post-administration change from the value prior to administration of a test compound.

Results of the measurement are shown in Table 4 below.

TABLE 4

| | Percent (%) Increased Blood Flow | | | |
|---|---|---|---|---|
| Compound No. | Vertebral artery | Common corotid artery | Femoral artery | Coronary artery |
| 5 | +101 | +66 | +65 | +101 |
| 6 | +73 | +17 | +61 | — |
| 7 | +45 | +16 | — | — |
| 14 | +59 | — | — | — |
| 15 | +40 | — | — | — |
| 16 | +50 | — | — | — |
| 30 | +92 | +32 | +65 | — |

Useful pharmaceutical dosage-forms for administration of the compounds of this invention are illustrated below.

| Tablets (per tablet) | |
|---|---|
| Methyl 6-(4-methyl-1-piperazinyl)nicotinate | 10 mg |
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct tableting. The powders were formed by means of a rotary tableting machine to tablets 6 mm in diameter each weighing 100 mg.

| Granules (per pack) | | |
|---|---|---|
| Methyl 6-(4-methyl-1-piperazinyl)nicotinate | 10 mg | |
| Lactose | 90 mg | A |
| Corn starch | 50 mg | |
| Crystalline cellulose | 50 mg | |
| Hydroxypropyl cellulose | 10 mg | B |
| Ethanol | 90 mg | |

Component A was uniformly blended, to which was added solution B. The mixture was kneaded. The kneaded mass was graded by the extrusion granulating method and then dried in a drier at 50° C. The dried granules were screened to a mesh range between 297 μm and 1460 μm to prepare granules. One pack weighed 200 mg.

| Syrups | |
|---|---|
| Methyl 6-(4-methyl-1-piperazinyl)nicotinate | 1.000 g |

| Syrups -continued | |
|---|---|
| White sugar | 30.000 g |
| D-Sorbitol 70 w/v % | 25.000 g |
| Ethyl paraoxybenzoate | 0.030 g |
| Propyl paraoxybenzoate | 0.015 g |
| Flavors | 0.200 g |
| Glycerin | 0.150 g |
| 96% Ethanol | 0.500 g |
| Distilled water | q.s. |
| | Total to 100 ml |

White sugar, D-sorbitol, methyl paraoxybenzoate, propyl paraoxybenzoate and the active ingredient were dissolved in 60 g of warm water. After cooling, a solution of the flavors in the glycerin and the ethanol was added. To the resulting mixture was added the water to 100 ml.

| Injections | |
|---|---|
| Methyl 6-(4-methyl-1-piperazinyl)nicotinate | 1 mg |
| Sodium chloride | 10 mg |
| Distilled water | q.s. |
| | Total to 1.0 ml |

Sodium chloride and the active ingredient were dissolved in distilled water to a total volume of 1.0 ml.

| Suppositories | |
|---|---|
| Methyl 6-(4-methyl-1-piperazinyl)nicotinate | 2 g |
| Polyethylene glycol 4000 | 20 g |
| Glycerin | 78 g |
| | Total to 100 g |

The active ingredient was dissolved in the glycerin. To the solution was added polyethylene glycol 4000 and the mixture was dissolved under heat. The solution was poured into a suppository mold to prepare suppositories each weighing 1.5 g.

What is claimed is:

1. A compound of formula (I)

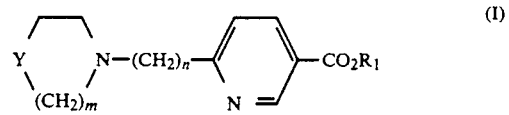

wherein
$R_1$ is hydrogen or $C_1$–$C_6$ alkyl;
Y is —$CH_2$—, —O—,

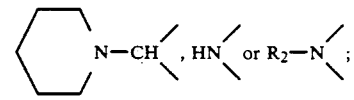

$R_2$ is $C_1$–$C_6$ alkyl; $C_2$–$C_6$ alkenyl; $C_3$–$C_6$ cycloalkyl; phenyl which may be mono- or di-substituted on the phenyl ring with $C_1$–$C_6$ alkoxy; aralkyl which may be mono- or di-substituted on the aromatic ring with $C_1$–$C_6$ alkoxy; diphenylmethyl; carbo($C_1$–$C_2$) alkoxy; or furanyl or pyrrolidinyl which is linked to the nitrogen atom via carbonyl or carbonylmethylene;

m is 2 or 3;

and n is 0 or 1, or a physiologically acceptable salt thereof.

2. A compound of claim 1 wherein $R_1$ is methyl, ethyl, n-propyl, i-propyl, n-butyl, i-butyl, tert-butyl or hexyl.

3. A compound of claim 1 wherein Y is

and $R_2$ is $C_1-C_6$ alkyl, $C_2-C_6$ alkenyl, $C_3-C_6$ cycloalkyl, diphenylmethyl or carbo $(C_1-C_2)$ alkoxy.

4. A compound of claim 3 wherein $R_2$ is methyl, ethyl, n-propyl, i-propyl, propenyl, cyclopentyl, cyclohexyl, methoxycarbonyl or ethoxycarbonyl.

5. A compound of claim 1 wherein Y is

and $R_2$ is phenyl which may be mono- or di-substituted on the phenyl ring with $C_1-C_6$ alkoxy; aralkyl which may be mono- or di-substituted on the aromatic ring with $C_1-C_6$ alkoxy; or furanyl or pyrrolidinyl which is linked to the nitrogen atom via carbonyl or carbonylmethylene.

6. A compound of claim 5 wherein $R_2$ is phenyl, methoxyphenyl, ethoxyphenyl, benzyl, phenylethyl, methoxybenzyl, ethoxybenzyl, 2-furancarbonyl or 1-pyrrolidinylcarbonylmethyl.

7. A pharmaceutical composition having a blood flow-increasing action which comprises a therapeutically effective amount of a compound of claim 1 or a physiologically acceptable salt thereof and a pharmaceutically acceptable carrier.

8. A pharmaceutical composition having a blood flow-increasing action which comprises a therapeutically effective amount of a compound of claim 2 or a physiologically acceptable salt thereof and a pharmaceutically acceptable carrier.

9. A pharmaceutical composition having a blood flow-increasing action which comprises a therapeutically effective amount of a compound of claim 3 or a physiologically acceptable salt thereof and a pharmaceutically 10. A pharmaceutical composition having a blood flow-increasing action which comprises a therapeutically effective amount of a compound of claim 4 or a physiologically acceptable salt thereof and a pharmaceutically acceptable carrier.

11. A pharmaceutical composition having a blood flow-increasing action which comprises a therapeutically effective amount of a compound of claim 5 or a physiologically acceptable salt thereof and a pharmaceutically acceptable carrier.

12. A pharmaceutical composition having a blood flow-increasing action which comprises a therapeutically effective amount of a compound of claim 6 or a physiologically acceptable salt thereof and a pharmaceutically acceptable carrier.

* * * * *